United States Patent
Ho

(10) Patent No.: US 8,777,882 B2
(45) Date of Patent: Jul. 15, 2014

(54) AIR TRACTION BELT STRUCTURE

(71) Applicant: Hoi Ming Michael Ho, Ontario (CA)

(72) Inventor: Hoi Ming Michael Ho, Ontario (CA)

(*) Notice: Subject to any disclaimer, the term of this patent is extended or adjusted under 35 U.S.C. 154(b) by 0 days.

(21) Appl. No.: 13/630,021

(22) Filed: Sep. 28, 2012

(65) Prior Publication Data

US 2014/0039369 A1 Feb. 6, 2014

(30) Foreign Application Priority Data

Jul. 31, 2012 (TW) .............................. 101214759 A

(51) Int. Cl.
*A61F 5/00* (2006.01)
*A61G 15/00* (2006.01)

(52) U.S. Cl.
USPC .............................. 602/13; 602/19; 128/845

(58) Field of Classification Search
CPC ...... A61F 13/14; A61H 9/0078; A61B 17/12; A61B 17/1325; A61B 17/135; A61B 17/132; A61B 17/1322
USPC ........................ 602/1, 5–6, 12–13, 17–20, 32; 606/240–241, 237, 201; 128/874–876, 128/96.1, 99.1, 100.1; 601/143
See application file for complete search history.

(56) References Cited

U.S. PATENT DOCUMENTS

| 5,421,809 A * | 6/1995 | Rise ................................ 602/19 |
| 5,980,560 A * | 11/1999 | Chang ........................... 606/241 |
| 8,012,113 B2 * | 9/2011 | Lee et al. ......................... 602/19 |
| 2006/0287621 A1 * | 12/2006 | Atkinson et al. .............. 601/151 |

* cited by examiner

*Primary Examiner* — Ophelia A Hawthorne
(74) *Attorney, Agent, or Firm* — Bacon & Thomas, PLLC

(57) ABSTRACT

The present invention is to provide an air traction belt structure, which includes an inner inflatable traction belt having an air valve thereon for communicating with an inflatable space therein and, and an outer solid support belt having a smaller width than the inner inflatable traction belt and movably surrounding outside of the inner inflatable traction belt. Since a first end of the outer solid support belt can pass through a through hole formed on the inner inflatable traction belt and extend to an inner side of the inner inflatable traction belt, a second end of the outer solid support belt can easily pass through a fixing ring provided on the first end of the outer solid support belt and be pulled by a user, for firmly tightening both the inflated inner inflatable traction belt and the outer solid support belt onto the user's waist at the same time.

5 Claims, 6 Drawing Sheets

AIR TRACTION BELT STRUCTURE

FIELD OF THE INVENTION

The present invention relates to an air traction belt structure, more particularly to an air traction belt including an outer solid support belt capable of movably surrounding an outer side of an inner inflatable traction belt and easily being pulled by a user, so as for the user to easily and firmly tighten the inflated inner inflatable traction belt onto the user's waist for enhancing the supporting, traction, stretching, decompression and protecting effects to the waist.

BACKGROUND OF THE INVENTION

According to a survey conducted in 1994 by the Centers for Disease Control and Prevention (CDC) of the United States regarding how medical aids were used in the US, 47.1% of traction belt users were 44 years old and under, 36.4% were 45~64 years old, and 16.5% were 65 years old and above. Traction belts—though less frequently used by those 65 years of age and above, who typically make more use of such personal mobility aids as walking sticks, walkers, and wheelchairs—are very important and common medical aids for other age groups.

The inventor of the present invention has found, after years of survey and research, that traction belts are often worn by office workers, computer users, those who handle heavy objects, and salespersons who are required to stand for a long time. These people use traction belts to support the lumbar region, with a view to reducing the pressure on the vertebral joints, lumbar spinal discs and the surrounding tissues, limiting the mobility of the lumbar vertebrae and the lower back, maintaining the normal lumbar curve, and correcting or adjusting body posture. Traction belts also serve to keep or increase abdominal pressure, alleviate the force acting on joints, decompress herniated lumbar spinal discs, relax muscles, reduce convulsions or spasms, and enhance blood circulation around back muscles to promote tissue recovery and relieve pain.

Most of the traction belts on the market are made of elastic fabrics, including nylon, LYCRA® fibers, and so on, but these traction belts generally do not provide the desired support, traction, decompression and protection. As an improved version, air traction belts were developed. FIGS. 1 and 2 illustrate an existing air traction belt 1 with an inflatable space formed therein. The outer side of the air traction belt 1 is connected with an air valve 12 to which an air pump can connect for the purpose of inflation. The outer and inner sides of the air traction belt 1 are respectively provided with fastening elements 10 and 11 (e.g., self-adhesive fabrics or VELCRO®). Once the air traction belt 1 is wrapped around the user's waist, the fastening elements 10 and 11 can be fastened to each other to provide a fixing effect. To use the air traction belt 1, it is necessary to wrap the fraction belt around the waist very tightly in advance before inflating the traction belt with air. The traction belt must be tightly secured around the waist in order to secure the lower portion of the traction belt to the user's pelvic crest, and secure the upper portion of the traction belt to the lower portion of the user's rib cage. When the traction belt is inflated with air, the traction belt will expand vertically by about 3.25 inches or 8 cm. If the traction belt is not wrapped around the user's waist very tightly, the upper and lower portion of the traction belt will slip against the user's body and this will render the traction belt useless as it will not provide the traction and decompression effects. Another problem with the traditional air traction belt is that it is soft and resilient even after it's fully inflated. Due to it's resiliency, it cannot provide adequate support.

To tighten the traditional air traction belt 1, the user has to apply a considerable force with both hands when tightening the air traction belt 1 and fastening the fastening elements 10 and 11. However, the inventor of the present invention has found that most users have problem completing this tightening and fastening action, and those who with relatively less physical agility and strength (e.g., the elderly and the sick) cannot complete this tightening and fastening action at all. Moreover, in tightening the air traction belt 1, the user's arms are folding inward and crossed awkwardly, which hinders force application. In addition, the great width of the air traction belt 1 makes it difficult for the user to grasp the air traction belt 1 and apply pulling forces thereto. As a result, many users cannot wrap the air traction belt 1 tight enough around the waist in order for the air traction belt 1 to provide sufficient support, traction and protection.

Besides, referring to FIG. 1, when the outlet valve 20 of the air pump is connected to the air valve 12 of the air traction belt 1, the two valves are held in the connected state only by a fixing clamp 21, which, according to the survey and research conducted by the inventor of the present invention however, cannot firmly connect the outlet valve 20 and the air valve 12 during the inflation process. Hence, with frequent leaks, the air pump cannot pump air into the air traction belt 1 efficiently. Not only does this inefficient pumping process result in a waste of time, but also the user may unknowingly use the air traction belt 1 in a not fully inflated state which provides inadequate support without having traction, stretching or decompression effect to the user's waist.

In addition, in the current market, when a consumer orders a fraction belt online or over telephone, he/she often get the fraction belt that does not fit him/her properly. Though the consumer can buy a fraction belt from a retail store, he/she may still pick up a traction belt that does not fit him/her since the salesclerk of the retail store does not know the user's waist size, and the users themselves often doesn't know what their correct waist sizes are. In fact, a traction belt that is too small cannot be wrapped around the waist, and a traction belt that is too loose will not provide support, traction, stretching and decompression to the consumer's waist, so the right size fitting is essential for the traction belt to provide any benefits to the consumer. In order to provide proper support and traction, an extension piece (such as VELCRO®) is supplied to the consumer for attaching to two ends of the traction belt and adjusting the length of the traction belt, so as to fit the consumer's waist. However, the biggest problem of the traditional traction belt is that it is extremely difficult for the manufacture thereof to design a size fitting every consumer's waist size. Thus, the traditional traction belts must be made in 6 different sizes, i.e. XS, S, M, L, XL and XXL, and each traction belt must be provided with an extension piece in order to fit all the different consumers' waist sizes.

Therefore, the issue to be addressed by the present invention is to overcome the various drawbacks of the conventional air traction belts and design an air traction belt to which a tightening force can be conveniently applied, thus allowing the elderly, the sick, and others with relatively less strength and agility to tighten the air traction belt with ease and receive sufficient support, traction, stretching, decompression and protection therefrom. The new design also combines two belts in one, a soft resilient air expandable traction belt on the inner layer and a rigid non giving support belt on the outer layer. The rigid non giving belt on the outer layer provides strong support when the air fraction belt is either deflated and inflated, while the soft resilient air expandable belt on the inner layer provides traction, stretching and decompression effects on the waist. The new design allows the user to use the air traction belt for support only, and/or for traction, stretching and decompression simultaneously. It is also desirable that the air traction belt does not leak during the inflation process.

BRIEF SUMMARY OF THE INVENTION

In view of the aforementioned drawbacks of the conventional air traction belts, the inventor of the present invention conducted extensive research and experiment and finally succeeded in developing an air traction belt structure as disclosed herein. The disclosed air traction belt structure is designed against leakage during inflation and can be easily tightened by a user with relatively less physical strength and agility. Consequently, the air traction belt structure features convenience of use and is enhanced in its supporting, traction, stretching, decompressing and protecting effects.

It is an object of the present invention to provide an air traction belt structure which includes an inner inflatable traction belt and an outer solid support belt. The inner inflatable traction belt forms an inflatable space therein. The outer side of the inner inflatable traction belt is provided with an air valve adjacent to one end of the inner inflatable traction belt, wherein the air valve communicates with the inflatable space. The inner inflatable traction belt is also formed with a through hole adjacent to the aforesaid end thereof. The outer solid support belt has a smaller width than the inner inflatable traction belt and can movably surround the outer side of the inner inflatable traction belt over an area corresponding to a transversely middle section of the inner inflatable traction belt. A first end of the outer solid support belt passes through the through hole of the inner inflatable traction belt, extends to the inner side of the inner inflatable traction belt, and is fixedly provided with a fastening ring. A second end of the outer solid support belt can pass through the fixing ring and be pulled so as to tighten the inner inflatable traction belt. The technical features of the present invention are such that, before inflating the inner inflatable traction belt, the second end of the outer solid support belt can be inserted through the fixing ring and forcefully pulled to tighten the outer solid support belt and the inner inflatable traction belt at the same time. By design, the outer solid support belt is fixed on the position between the upper portion and the lower portion of the inner inflatable traction belt. This design enables the upper portion of the inner inflatable traction belt to tighten against the user's lower rid cage, and enables the lower portion of the inner inflatable traction belt to tighten against the user's pelvic crest. Simultaneously, the tightening of the outer solid support belt will create a tightening effect around the mid section of outer circumference of the inner inflatable traction belt. This prevents lateral expansion of the otherwise resilient inner inflatable traction belt to provide strong support to the user's waist. Once the outer solid support belt and inner inflatable traction belt are tightened around the user's waist, the user can now inflate the inner inflatable traction belt to cause traction, stretching and decompression effect on the user's lower back.

Once the inner inflatable traction belt is inflated and wrapped around the user's waist, the second end of the outer solid support belt can be inserted through the fixing ring and forcefully pulled to tighten the outer solid support belt, thereby tightening the transversely middle section of the inner inflatable traction belt. Thus, the transversely middle section of the inner inflatable traction belt is pressed tightly against, and produces a tightening effect on, the user's waist.

As the user can tighten the outer solid support belt by applying a pulling force thereto with an outwardly extending arm, and the outer solid support belt has a reduced width, even one who has relatively less physical strength (e.g., an elderly or sick person) and poor agility can easily pull the outer solid support belt tight to tighten both the inner inflatable traction belt and the outer solid support belt simultaneously. Due to the length and the large range of adjustable fastening positions of the outer solid support belt, the traction belt of this invention no more needs an extension piece for increasing the length thereof and making the fraction belt fit the consumer's waist properly. The traction belt of this invention can be easily designed to properly fit all waist sizes without the use of an extension piece. Alternatively, the traction belt of this invention can be made in 2 sizes, i.e. size A and size B, wherein Size A fits all waist sizes from extra small to medium, and Size B fits all waist sizes from large to extra large. It will be easy for the consumer to select the right traction belt even if he/she doesn't exactly know the waist size thereof. In addition, the outer solid support belt will continue to make the traction belt of this invention fit the consumer when the waist size of the consumer changes due to weight gain or loss, and even as waist size change before and after meal, and when the user changes from standing to sitting position. In comparison with the 6 sizes of the traditional traction belt mentioned in the prior art, the traction belt of this invention only needs 2 sizes for providing proper support and traction to all the consumers with different waist sizes and effectively relieving their back pain and instability accordingly.

Another object of the present invention is to provide the foregoing air traction belt structure, wherein the inner side of the inner inflatable traction belt is provided with two elastic support bands respectively adjacent to the two transverse edges of the inner inflatable traction belt. The elastic support bands are intended to provide an elastic and stable support to the areas below and above the tightened portion of the waist.

Still another object of the present invention is to provide the foregoing air traction belt structure, wherein the inner surface of each of the elastic support bands has a friction coefficient lower than that of the inner surface of the inner inflatable traction belt. Thus, when the transversely middle section of the inner inflatable fraction belt is pressed tightly against the user's waist, the areas below and above the tightened portion of the waist are elastically and stably supported by the elastic support bands, the friction between the inner surfaces of the elastic support bands and the areas below and above the tightened portion of the waist is substantially reduced to effectively increase the mobility of the user's waist and the comfort of the waist during movement.

Yet another object of the two elastic support bands is how they are attached to the inner inflatable traction belt. When force is used to tighten the outer solid support belt, the force is also applied to the upper and lower elastic support bands to tighten them against the user's body. These two elastic support bands are made with material having a friction coefficient lower than that of the inner surface of the inner inflatable traction belt, when the outer solid support belt is tightened, the outer solid support belt will grip tightly to secure the inner inflatable traction belt against the user's body. As the inner inflatable traction belt is inflated, it expands vertically to provide the traction, stretching and decompression effect, which can only occur if the top and bottom portion of the inner inflatable traction belt is secured tightly against the user's body.

Yet another object of the present invention is to provide the foregoing air traction belt structure, wherein one end of the air valve is externally threaded in order to make secure threaded connection with the outlet valve of an air pump, thus allowing the air pump to inflate the inflatable space and, at the same time, preventing leakage during the inflation process.

Another object of the present invention is to provide the foregoing air traction belt structure, wherein the fixing ring has a width greater than the through hole. This prevents the fixing ring from displacement or even passing through the through hole when the outer solid support belt is pulled tight. Consequently, the outer solid support belt, once pulled tight, is kept from falling off.

A further object of the present invention is to provide the foregoing air traction belt structure, wherein the inner side of the inner inflatable fraction belt is extended with at least one limiting portion adjacent to the through hole. Each limiting portion has one end connected to the first end of the outer solid support belt or the fixing ring. Thus, it can be ensured that, once the outer solid support belt is pulled tight, both the first end of the outer solid support belt and the fixing ring stay on the inner side of the inner inflatable traction belt.

BRIEF DESCRIPTION OF THE SEVERAL VIEWS OF THE DRAWINGS

The structure as well as a preferred mode of use, further objects, and advantages of the present invention will be best understood by referring to the following detailed description of an illustrative embodiment in conjunction with the accompanying drawings, in which.

DETAILED DESCRIPTION OF THE INVENTION

The inventor of the present invention has long been engaged in research and development in the medical aid-related fields. In the process, the inventor has found that the conventional air traction belts are very likely to press only loosely against the waist and hence fail to provide the desired support, traction, stretch, decompression and protection. This is not only because the tightening and fastening action required is difficult to perform by those with relatively less physical strength and agility, but also because the conventional air traction belts are too wide to be grasped and pulled. Although attempts have been made to solve the aforesaid problems by further improving the structures of the conventional air traction belts, an ideal solution has yet to be found. In consideration of this, the inventor came up with the idea of movably surrounding an inner inflatable traction belt with an outer solid support belt. Thus, by pulling tight the outer solid support belt, the inner inflatable traction belt can be tightened around the user's waist, thereby solving the problems of the conventional air traction belts.

Figure 1:
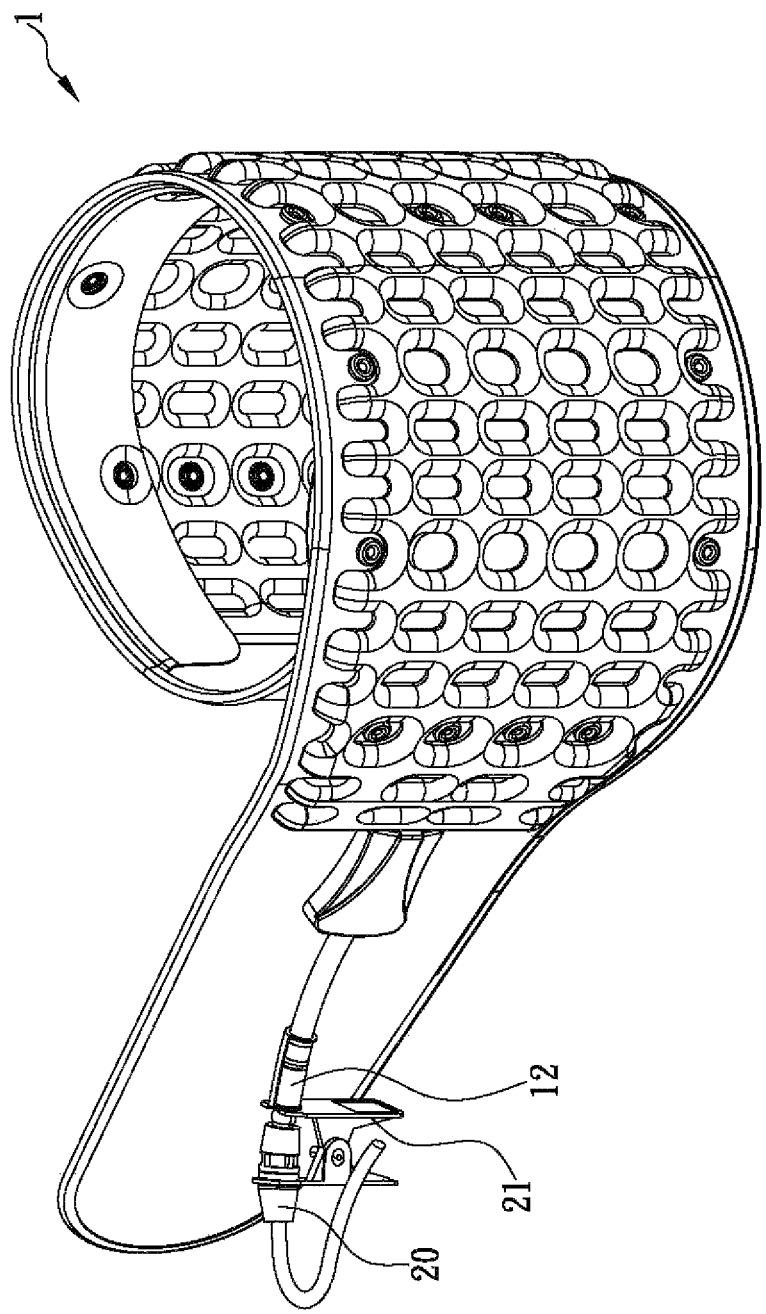
FIG. 1 is a perspective view of a conventional air traction belt.
Figure 2:
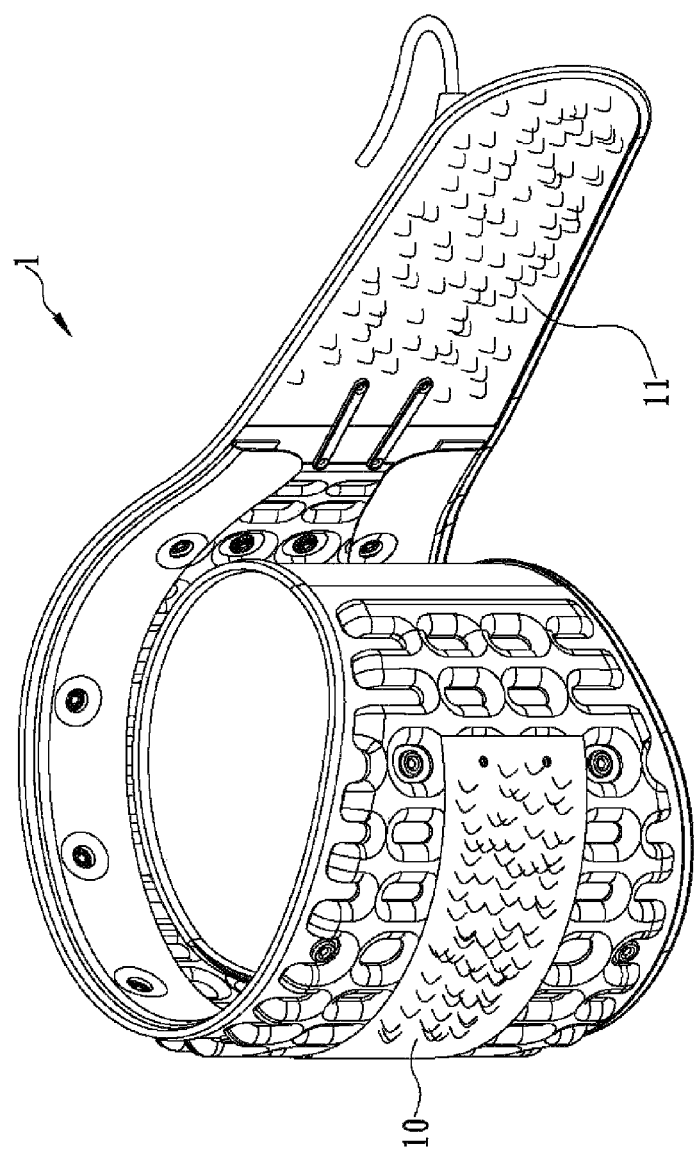
FIG. 2 is another perspective view of the convention air traction belt shown in FIG. 1.
Figure 3:
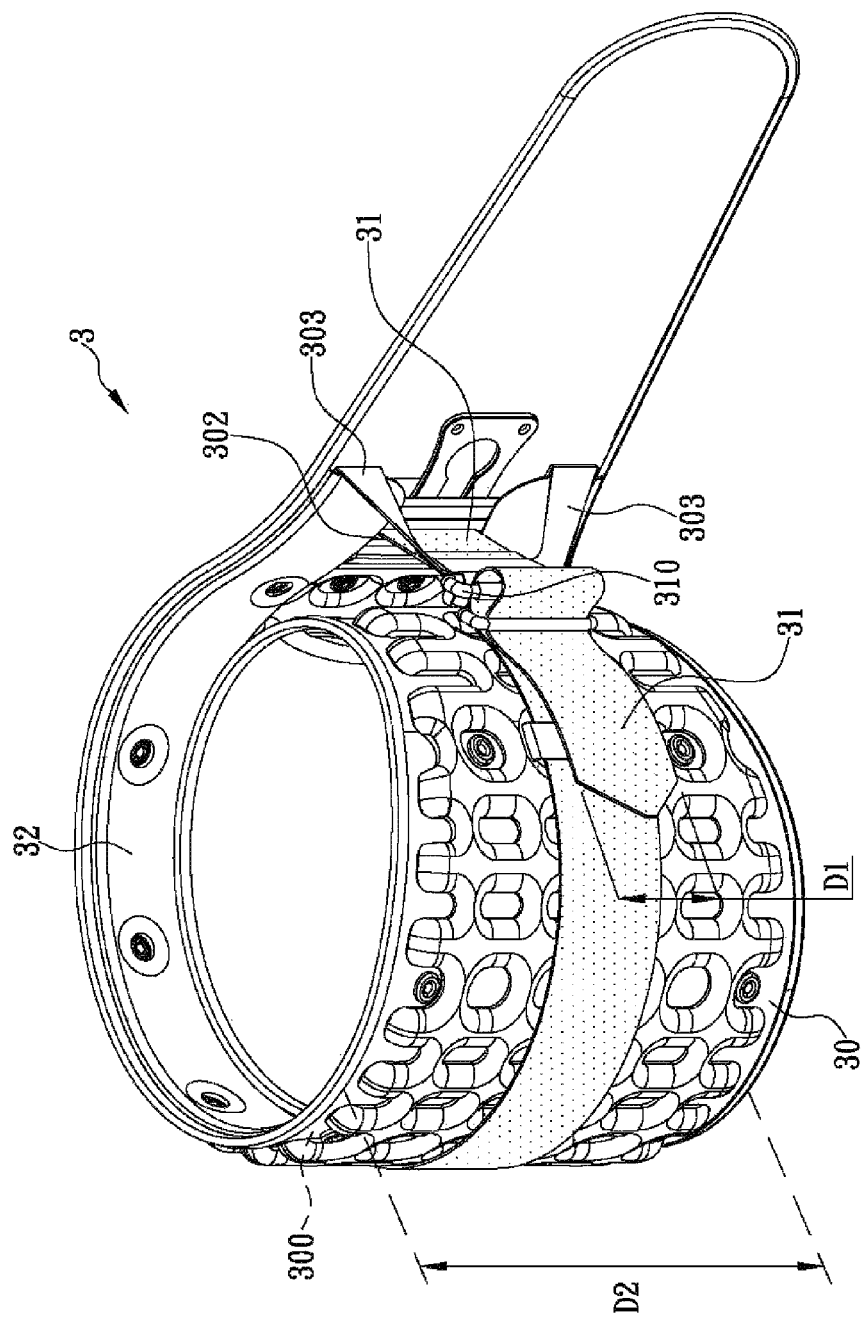
FIG. 3 is a perspective view of a preferred embodiment of the present invention.
Figure 4:
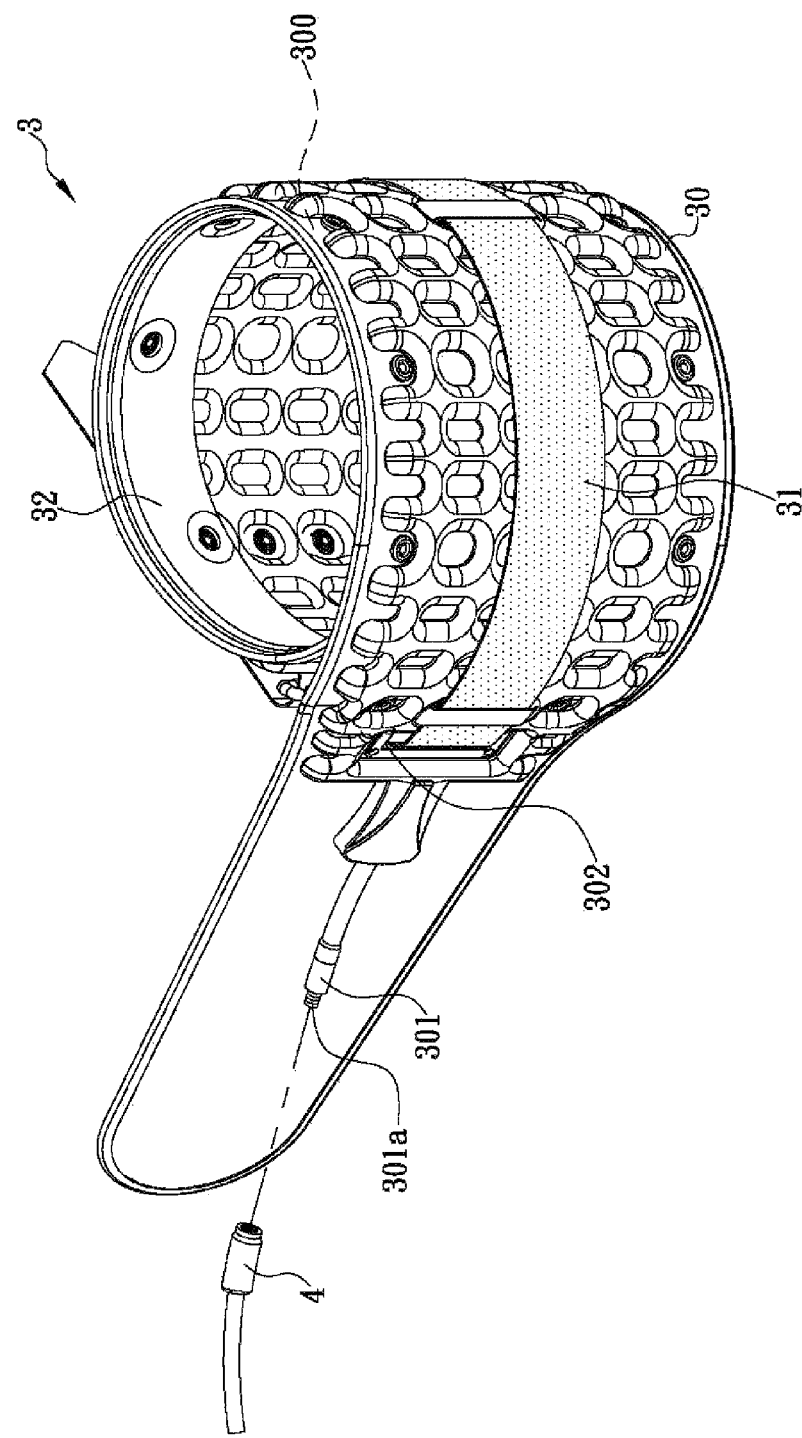
FIG. 4 is another perspective view of the preferred embodiment of the present invention.

The present invention discloses an air traction belt structure. In a preferred embodiment of the present invention as shown in FIGS. 3 and 4, the air traction belt structure 3 includes an inner inflatable traction belt 30 and an outer solid support belt 31, wherein the inner inflatable fraction belt 30 forms an inflatable space 300 therein. In this preferred embodiment, the inner inflatable traction belt 30 is constructed by plural layers (e.g., four layers) of thermoplastic polyurethane (TPU) sandwiched between fabric layers. To make the inner inflatable traction belt 30, the plural layers of TPU can be connected by ultrasonic welding, and the inflatable space 300 in the inner inflatable traction belt 30 can be formed as a network of airtight tubules such that, once the inflatable space 300 of the inner inflatable traction belt 30 is filled with air, the inner inflatable traction belt 30 is uniformly flexible and can provide uniform support. However, the present invention imposes no limitations on the making of the inner inflatable traction belt 30. The materials and manufacturing method of the inner inflatable traction belt 30 may vary, and the structural design of the inflatable space 300 may be adjusted, based on user requirements or design considerations. All changes and modifications readily conceivable by a person skilled in the art should fall within the scope of the present invention.

Referring to FIG. 4, the outer side of the inner inflatable traction belt 30 is provided with an air valve 301 adjacent to one end of the inner inflatable traction belt 30. The air valve 301 communicates with the inflatable space 300 and has one end externally provided with threads 301a such that the outlet valve 4 of an air pump can be threadedly and securely connected to the air valve 301 to inflate the inflatable space 300. As shown in FIG. 3, the inner side of the inner inflatable traction belt 30 (i.e., the side to press against the user' body) is provided with two elastic support bands 32 respectively adjacent to the two transverse edges of the inner inflatable traction belt 30. In addition, a through hole 302 is formed on the inner inflatable traction belt 30 adjacent to the aforesaid end thereof (i.e., the end adjacent to which the air valve 301 is provided).

In the preferred embodiment of the present invention as shown in FIG. 3, the width D1 of the outer solid support belt 31 is less than the width D2 of the inner inflatable traction belt 30, and the outer solid support belt 31 can movably surround the outer side of the inner inflatable traction belt 30 over an area corresponding to the transversely middle section of the inner inflatable traction belt 30. The outer solid support belt 31 has a first end passing through the through hole 302 of the inner inflatable traction belt 30, extending to the inner side of the inner inflatable traction belt 30, and fixedly provided with a fixing ring 310. A second end of the outer solid support belt 31 can pass through the fixing ring 310 and be pulled to tighten the inner inflatable traction belt 30. The fixing ring 310 has a width greater than the through hole 302 and therefore will not displace or even pass through the through hole 302 when the outer solid support belt 31 is pulled tight. It is thus ensured that the outer solid support belt 31 will not fall off when pulled tight. Furthermore, the inner side of the inner inflatable traction belt 30 is extended with at least one limiting portion 303 adjacent to the through hole 302. In this preferred embodiment, the number of the at least one limiting portion 303 is two, and yet the present invention imposes no limitations in this regard. Each limiting portion 303 has one end connected to the first end of the outer solid support belt 31 or the fixing ring 310 to ensure that, once the outer solid support belt 31 is pulled tight, both the first end of the outer solid support belt 31 and the fixing ring 310 remain on the inner side of the inner inflatable traction belt 30.

Referring again to FIGS. 3 and 4, the technical features of the present invention are such that, before inflating the inner inflatable traction belt 30, the second end of the outer solid support belt 31 can be inserted through the fixing ring 310 and forcefully pulled to tighten the outer solid support belt 31 and the inner inflatable traction belt 30 at the same time. By design, the outer solid support belt 31 is fixed on the position between the upper portion and the lower portion of the inner inflatable traction belt 30. This design enables the upper portion of the inner inflatable traction belt 30 to tighten against the user's lower rid cage, and enables the lower portion of the inner inflatable traction belt 30 to tighten against the user's pelvic crest. Simultaneously, the tightening of the outer solid support belt 31 will create a tightening effect around the mid section of outer circumference of the inner inflatable traction belt 30, and prevent lateral expansion of the otherwise resilient inner inflatable traction belt 30 and then provide strong support for the waist. Once the outer solid support belt 31 and inflatable traction belt 30 is tightened around the user's waist, the user can now inflate the inner inflatable traction belt 30 to cause traction, stretching and decompression effect on the user's lower back.

Figure 5:
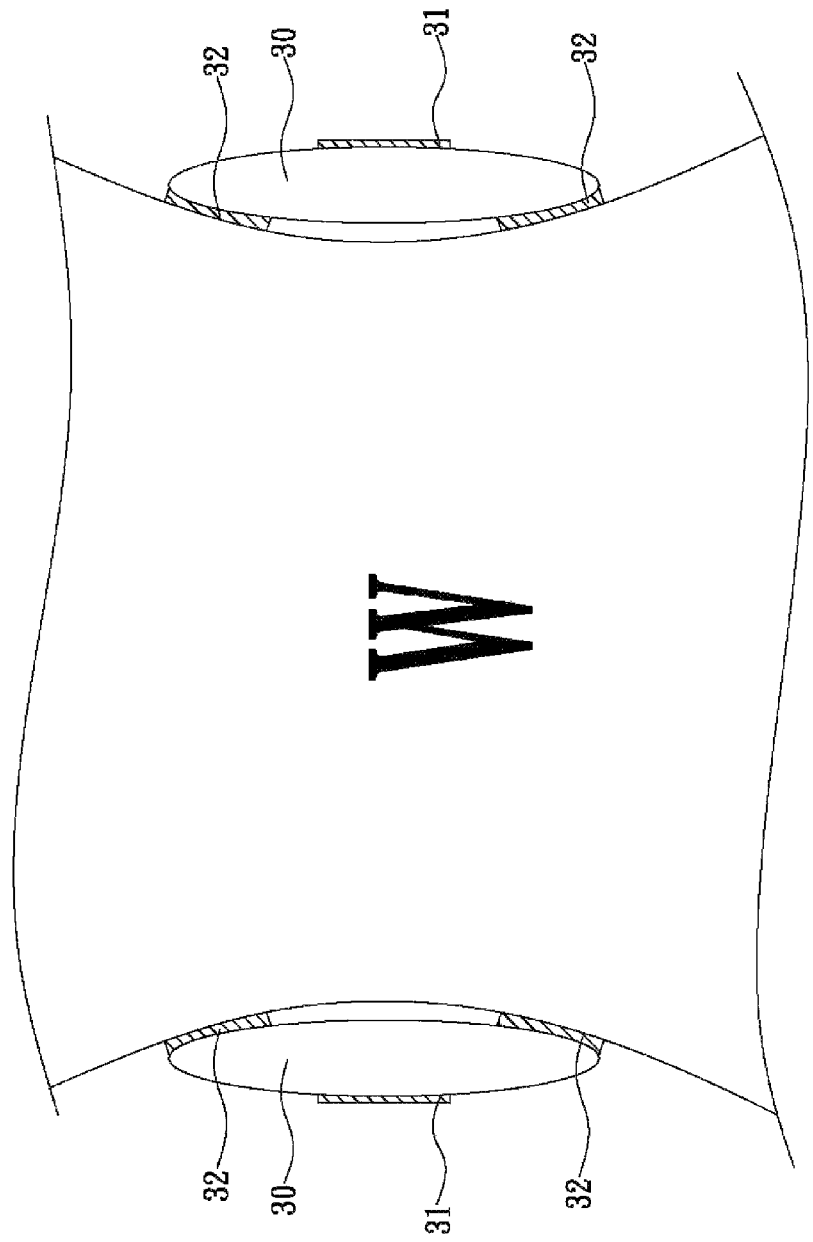
FIG. 5 schematically shows the air traction belt structure of the present invention before it is tightened up.
Figure 6:
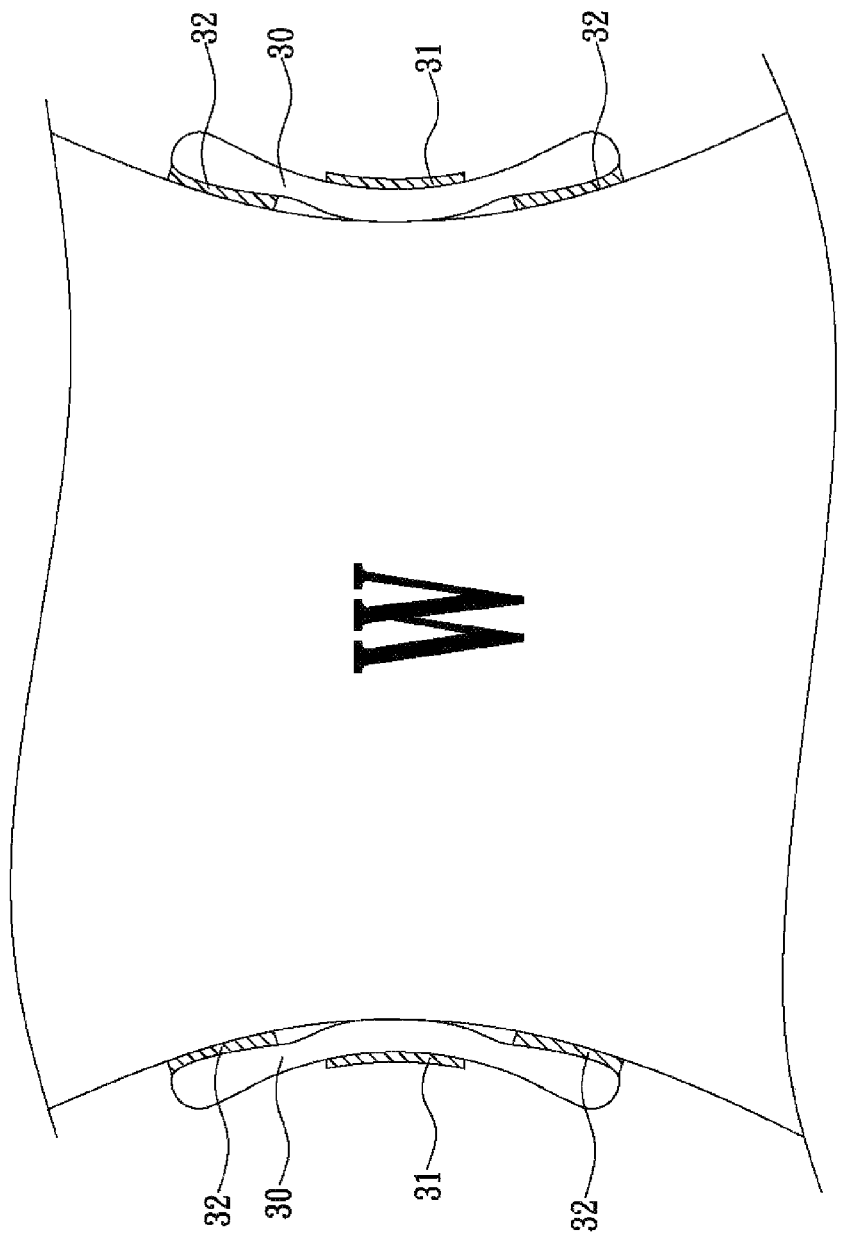
FIG. 6 schematically shows the air traction belt structure of the present invention after it is tightened up for use.

The technical features of the present invention allow a user to inflate the inner inflatable traction belt 30, wrap it around the waist, and then insert the second end of the outer solid support belt 31 through the fixing ring 310. By pulling the second end of the outer solid support belt 31 forcefully, the transversely middle section of the inner inflatable fraction belt 30 is tightened and hence pressed tightly against the user's waist. As a result, a tightening effect is produced on the user's waist. FIG. 5 shows a state before the inner inflatable traction belt 30 is tightened by the outer solid support belt 31. Once the transversely middle section of the inner inflatable traction belt 30 is tightened by the outer solid support belt 31, as shown in FIG. 6, the outer solid support belt 31 applies a pressure on the transversely middle section of the inner inflatable fraction belt 30. Consequently, the air in the inflatable space 300 is squeezed toward the transverse edges of the inner inflatable fraction belt 30 and causes the elastic support bands 32 to elastically and stably support the areas below and above the tightened portion of the waist W, thereby preventing the transverse edges of the inner inflatable traction belt 30 from rubbing against the user's waist W. Moreover, the inner surface of each elastic support band 32 has a friction coefficient lower than that of the inner surface of the inner inflatable traction belt 30, and the two elastic support bands 32 are fixed to the inner inflatable traction belt 30, such that the tightening of the outer solid support belt 31 will cause tightening of the inner inflatable fraction belt 30 against the user's body to minimize slippage. The friction between the inner surfaces of the elastic support bands 32 and the areas below and above the tightened portion of the waist W will be significantly reduced when the transversely middle section of the inner inflatable traction belt 30 is pressed tightly against the user's waist W and the areas below and above the tightened portion of the waist W are supported by the elastic support bands 32. As such, the mobility of the user's waist W is effectively enhanced, and so is the comfort of the waist W during movement.

Referring to FIG. 3, as the second end of the outer solid support belt 31 is designed to be pulled away from the user's body after insertion through the fixing ring 310, the user can tighten the outer solid support belt 31 by applying a pulling force thereto with an outwardly extending arm, rather than by applying opposite pulling forces with inwardly folding arms as is conventionally required. Therefore, even those with relatively less physical strength (e.g., the elderly and the sick) and agility can easily tighten the outer solid support belt 31 and thereby tighten the inner inflatable traction belt 30. In addition, the smaller width D1 of the outer solid support belt 31 facilitates grasping, so the outer solid support belt 31 can be pulled tight conveniently. Moreover, referring to FIG. 4, the external threads 301a at one end of the air valve 301 enable secure threaded connection to the outlet valve 4 of the air pump and thus prevent leaking during the inflation process.

While the invention herein disclosed has been described by means of specific embodiments, numerous modifications and variations could be made thereto by those skilled in the art without departing from the scope of the invention set forth in the claims.

What is claimed is:

1. An air traction belt structure, comprising:
    an inner inflatable traction belt forming an inflatable space therein; wherein the inner inflatable traction belt has an outer side provided with an air valve adjacent to an end of the inner inflatable traction belt, and the air valve is in communication with the inflatable space such that the inflatable space can be inflated through the air valve; wherein the inner inflatable traction belt is formed with a through hole adjacent to the end of the inner inflatable traction belt; and
    an outer solid support belt having a width smaller than that of the inner inflatable fraction belt and configured for movably surrounding the outer side of the inner inflatable traction belt over an area corresponding to a transversely middle section of the inner inflatable traction belt; wherein the outer solid support belt has a first end passing through the through hole of the inner inflatable traction belt, extending to an inner side of the inner inflatable traction belt and fixedly provided with a fixing ring, and a second end configured to pass through the fixing ring such that the inner inflatable traction belt can be tightened by pulling the second end of the outer solid support belt; wherein the fixing ring has a width greater than the through hole, and the inner side of the inner inflatable traction belt adjacent to the through hole is extended with at least a limiting portion, and the limiting portion has an end connected to the first end of the outer solid support belt or the fixing ring.

2. The air fraction belt structure of claim 1, wherein the inner side of the inner inflatable traction belt is provided with two elastic support bands respectively adjacent to two transverse edges of the inner inflatable traction belt, and the two elastic support bands are fixed to the inner inflatable traction belt, such that the tightening of the outer solid support belt will cause tightening of the two elastic support bands against a user's body.

3. The air traction belt structure of claim 2, wherein the air valve has an end externally provided with threads so as to connect threadedly and securely to an outlet valve of an air pump.

4. The air traction belt structure of claim 3, wherein an inner surface of each said elastic support band has a friction coefficient lower than that of an inner surface of the inner inflatable traction belt.

5. The air traction belt structure of claim 4, wherein the inflatable space is formed as a network of airtight tubules.

* * * * *